US009999719B2

(12) United States Patent
Kitchen

(10) Patent No.: US 9,999,719 B2
(45) Date of Patent: Jun. 19, 2018

(54) CLAMP FOR AN IV PUMP

(71) Applicant: Laurie Kitchen, Columbia Falls, MT (US)

(72) Inventor: Laurie Kitchen, Columbia Falls, MT (US)

( * ) Notice: Subject to any disclaimer, the term of this patent is extended or adjusted under 35 U.S.C. 154(b) by 0 days. days.

(21) Appl. No.: 15/239,266

(22) Filed: Aug. 17, 2016

(65) Prior Publication Data

US 2017/0049956 A1 Feb. 23, 2017

Related U.S. Application Data

(60) Provisional application No. 62/206,113, filed on Aug. 17, 2015.

(51) Int. Cl.
*A47B 96/06* (2006.01)
*A61M 5/14* (2006.01)
*F16B 2/10* (2006.01)

(52) U.S. Cl.
CPC ............. *A61M 5/1415* (2013.01); *F16B 2/10* (2013.01)

(58) Field of Classification Search
CPC ............ A47K 1/08; A45F 5/02; F16M 13/022
See application file for complete search history.

(56) References Cited

U.S. PATENT DOCUMENTS

| 2,667,678 | A | * | 2/1954 | Hargrave | ................ B42F 1/006 24/508 |
| 4,844,397 | A | | 7/1989 | Skakoon et al. | |
| 5,135,189 | A | * | 8/1992 | Ghazizadeh | ........... F16M 11/40 248/104 |
| 5,322,253 | A | | 6/1994 | Stevens | |
| 5,829,723 | A | | 11/1998 | Brunner et al. | |
| 6,598,268 | B1 | * | 7/2003 | Zelman | ..................... A45F 5/02 24/13 |
| 7,766,313 | B2 | * | 8/2010 | Panosian | ................. B25B 5/003 269/3 |
| 7,850,329 | B2 | * | 12/2010 | Henry | ....................... F21L 4/04 362/191 |
| 7,980,521 | B2 | | 7/2011 | Harr et al. | |
| 8,020,825 | B2 | | 9/2011 | Dostaler et al. | |
| 8,128,046 | B1 | * | 3/2012 | Howard, Jr. | ............... A45F 5/02 224/930 |
| 8,256,984 | B2 | | 9/2012 | Fathallah et al. | |
| 8,695,957 | B2 | | 4/2014 | Quintania et al. | |
| 9,341,308 | B2 | * | 5/2016 | Lacy | ................... F16M 13/022 |
| 9,657,893 | B2 | * | 5/2017 | Buresh, II | ............ F16M 13/022 |
| 2011/0192951 | A1 | * | 8/2011 | Gooch | ................... F16M 11/12 248/316.7 |
| 2014/0007408 | A1 | | 1/2014 | Nool | |
| 2015/0090845 | A1 | | 4/2015 | Trelford et al. | |

(Continued)

*Primary Examiner* — Amy J. Sterling
(74) *Attorney, Agent, or Firm* — Parsons Behle & Latimer

(57) ABSTRACT

A clamp assembly for an IV pump, or similar device, is disclosed. Disclosed embodiments include a clamp having a first lever arm with a first clamping end and a second lever arm having a second clamping end. A central axle connects the first lever arm and the second lever arm and allows the first clamping end and the second clamping end to pivot away from and towards each other. A biasing spring biases the first clamping end towards the second clamping end. Also disclosed is a bracket that is connected to the first lever arm and has a pump mounting portion that allows an IV pump, or similar device, to be mounted thereon.

14 Claims, 4 Drawing Sheets

(56) References Cited

U.S. PATENT DOCUMENTS

| | | | |
|---|---|---|---|
| 2015/0090849 A1* | 4/2015 | Breitweiser | F16M 11/04 248/230.1 |
| 2015/0198283 A1 | 7/2015 | Lacy | |
| 2015/0219131 A1 | 8/2015 | Quintania et al. | |
| 2015/0224256 A1 | 8/2015 | Lee | |

* cited by examiner

CLAMP FOR AN IV PUMP

FIELD OF THE DISCLOSURE

This disclosure relates to clamps. More particularly, this disclosure relates to a clamp for an intravenous (IV) pump.

BACKGROUND

An IV pump typically needs to be attached to a pole, bed-rail, or other support bracket. Existing clamps for attachment are typically "C-type" clamps that require the user to turn, or screw-in, a post or screw that then captures the pole in between the screw end and a flattened surface on the "C" portion of the clamp. It is often inconvenient and time-consuming to adjust the screw and often requires a person to use both hands to properly fasten, adjust, or unfasten the clamp. Other drawbacks of existing IV pump attachment systems also exist.

SUMMARY

Accordingly, disclosed embodiments address the above-noted and other drawbacks of existing systems. In addition, disclosed embodiments provide a simple and easily operated clamp that enables attachment of an IV pump to a pole, bracket, stand, or other support.

In some embodiments, the clamp comprises two generally straight lever arms mounted about a central fulcrum axis and having a spring or other biasing component in-between the lever arms that causes the lever arms be urged together and to grip and hold a support. Embodiments also include reciprocal curved portions at the clamping ends of the lever arms that may facilitate the gripping of the clamp about a cylindrical pole or support.

In some embodiments, the clamp comprises a bracket mounted to one of the lever arms to enable mounting of an IV pump to the clamp. Other embodiments also exist.

Figure 1:
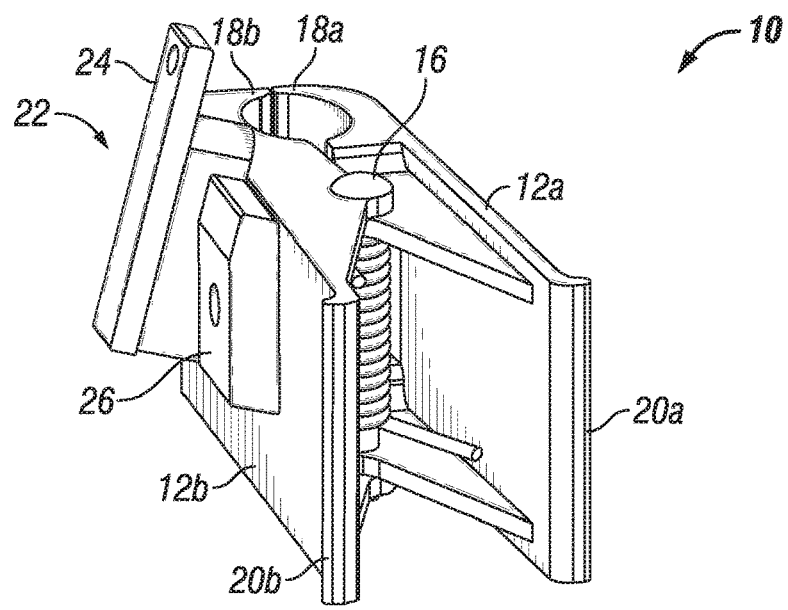
FIG. 1 is an isometric rear-side view of a clamp assembly in accordance with disclosed embodiments.
Figure 2:
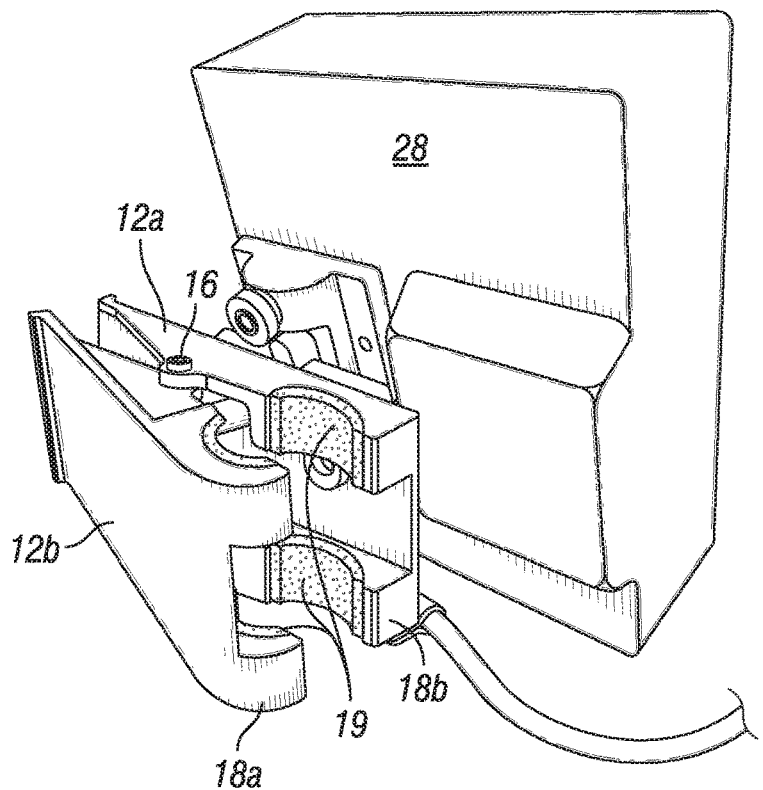
FIG. 2 is an isometric front-side view of a clamp assembly with the clamping ends open in accordance with disclosed embodiments.
Figure 3:
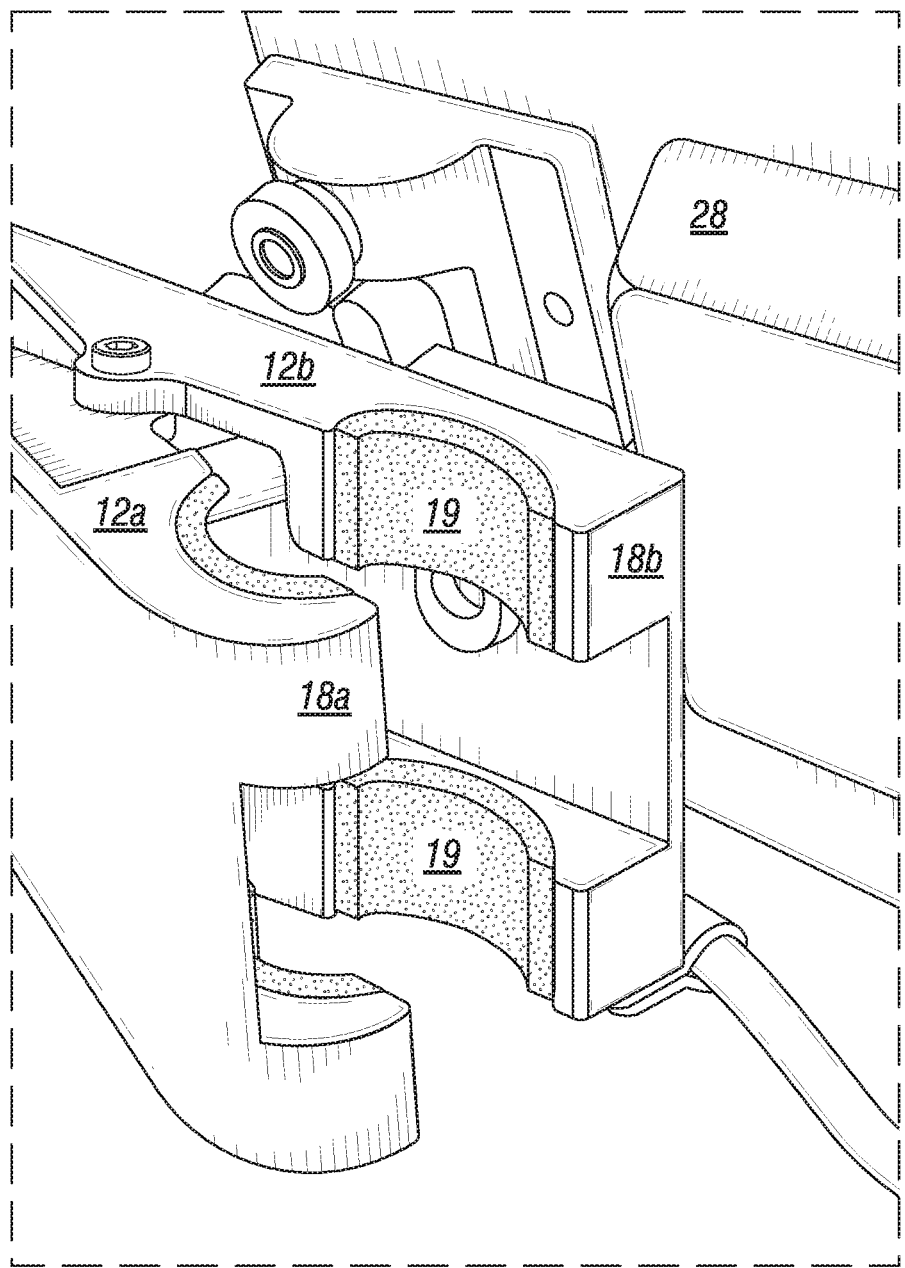
FIG. 3 is an isometric front-side, close-up view of a clamp assembly with the clamping ends open in accordance with disclosed embodiments.
Figure 4:
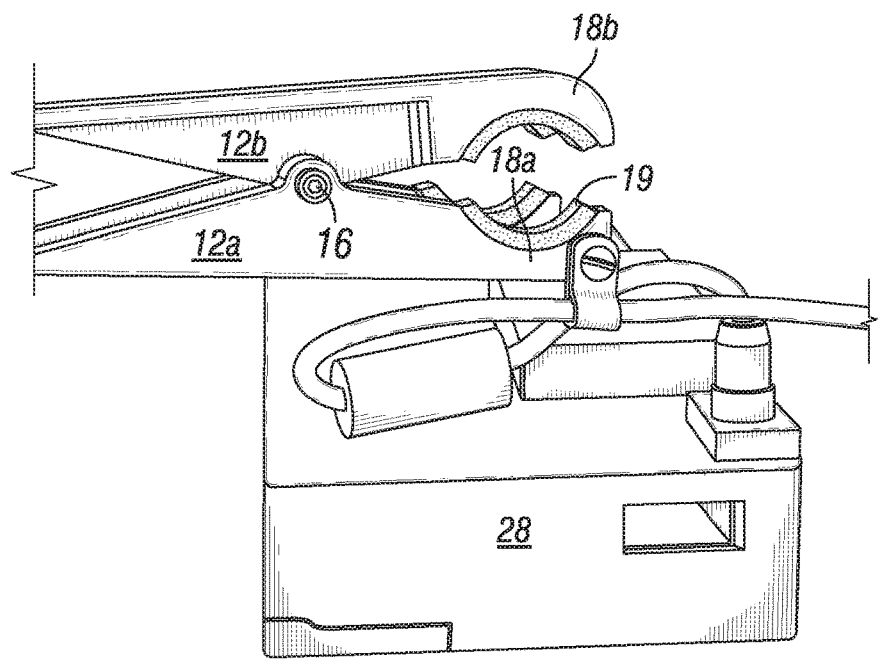
FIG. 4 is a top-side view of a clamp assembly with the clamping ends open in accordance with disclosed embodiments.

While the disclosure is susceptible to various modifications and alternative forms, specific embodiments have been shown by way of example in the drawings and will be described in detail herein. However, it should be understood that the disclosure is not intended to be limited to the particular forms disclosed. Rather, the intention is to cover all modifications, equivalents and alternatives falling within the spirit and scope of the invention as defined by the appended claims.

DETAILED DESCRIPTION

Figure 5:
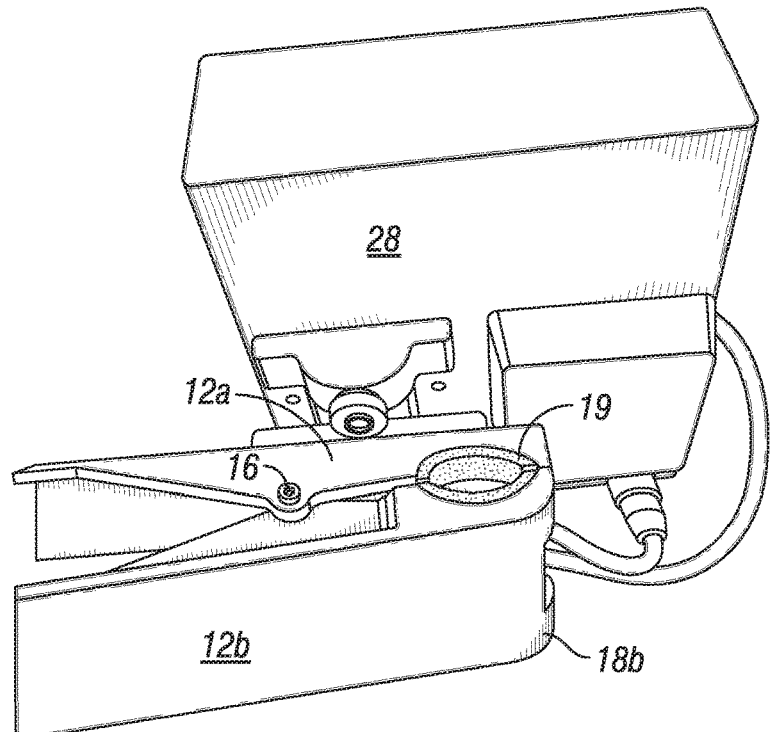
FIG. 5 is an isometric, top-side view of a clamp assembly with the clamping ends closed in accordance with disclosed embodiments.
Figure 6:
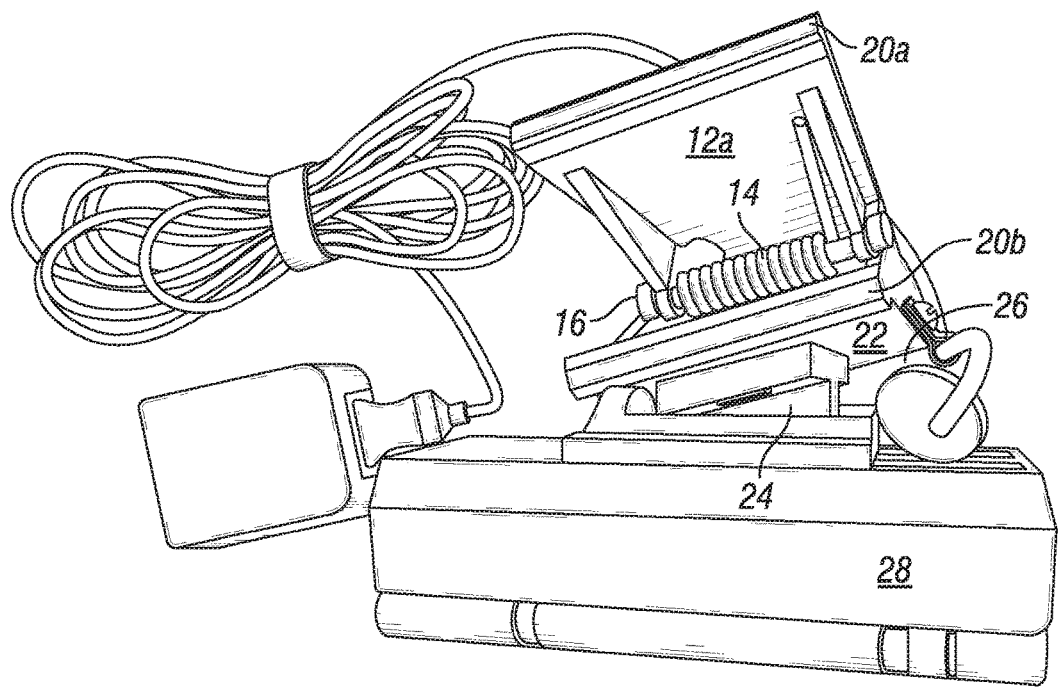
FIG. 6 is an isometric back-side view of a clamp assembly attached to an IV pump in accordance with disclosed embodiments.

As shown in FIG. 1, clamp assembly 10 may include a first lever arm 12a and a second lever arm 12b. Lever arms 12a and 12b may be mounted about a central axle or pin 16 and a biasing spring 14 may also be mounted thereon. The lever arms 12a and 12b are free to pivot about central axle 16. Ends of the biasing spring 14 engage the undersides of lever arms 12a and 12b and through the tension in the spring 14 bias the ends of lever arms 12a, 12b together as shown, for example, in FIGS. 1 and 5. While biasing spring 14 is shown as a coiled torsion spring, other types of biasing may also be used. For example, a leaf spring, a clock-type spring, or the like may be used provided sufficient biasing force is generated to effectively hold the clamp assembly 10 in the desired place.

In some embodiments, clamp assembly 10 may include reciprocally curved portions, clamping ends 18a and 18b, in the clamping end of the lever arms 12a and 12b, respectively. As further illustrated in FIGS. 2-5, gripping elements 19, such as rubber, plastics, textures (e.g., ribs, teeth, or knurling), or the like may be included in the clamping ends 18a, 18b to facilitate the gripping of the clamp assembly 10 to the support. In addition, while generally circular curves for clamping ends 18a and 18b are shown, the disclosure is not so limited and other shapes may also be employed. For example, triangular, or rectangular profiles may be employed for clamping ends 18a, 18b in order to clamp to poles or supports with correspondingly triangular or rectangular shape.

In some embodiments, lips 20a, 20b may be included at the rear, non-clamping end of the clamp 10. Lips 20a, 20b, may, among other things, facilitate the easy grasping of the clamp 10 when in operation to move the lever arms 12a, 12b together and open the clamping ends (18a, 18b) of the clamp 10. Again, other shapes and sizes of lips 20a, 20b may be used.

Clamp 10 may also include a bracket 22 that enables an IV pump 28, or other similar device, to be attached to the clamp assembly 10 as shown in FIGS. 2-6. Bracket 22 may include a pump mounting portion 24 that attaches to the IV pump 28, or similar device, and a clamp mounting portion 26 that attaches to one of the lever arms (e.g., 12b, as shown). Bracket 22 may be attached to the clamp 10 in any suitable manner. For example, bracket 22 may be glued, soldered, welded, screwed into place, or may fit into a mating notch or rib on the clamp 10. Likewise, pump mounting portion 24 may be attached to the IV pump 28, or similar device, in any suitable fashion.

As should be understood, the pump mounting portion 24 and the clamp mounting portion 26 are advantageously positioned with respect to one another to enable the IV pump 28, or similar device, to be mounted on the clamp assembly 10 in such a manner that the IV pump 28, or similar device, is in a conveniently useable orientation when mounted to the pole or other support. For example, pump mounting portion 24 and clamp mounting portion 26 may be mounted at different angles with respect to one another as show, for example, in FIG. 1.

FIGS. 2-6 show various views of embodiments of the clamp 10 attached to, for example, an IV pump 28. As also shown, in operation a user squeezes the ends of lever arms 12a, 12b together, potentially by using her fingers to grasp lips 20a, 20b. The squeezing together of the lever arms 12a, 12b causes the clamping end 18a, 18b, to open and release the mounting pole or bracket (not shown). When the user stops squeezing the lever arms 12a, 12b, the spring 14 biases the clamping ends 18a, 18b back together and grip the pole or mounting bracket. In such a manner, a user can use a single hand to attach, adjust, or remove the clamp assembly 10. In general, the clamping ends 18a, 18b are arranged to clamp a vertical pole or the like and position an IV pump 28, or similar device, in the proper orientation for use.

Figure 7:
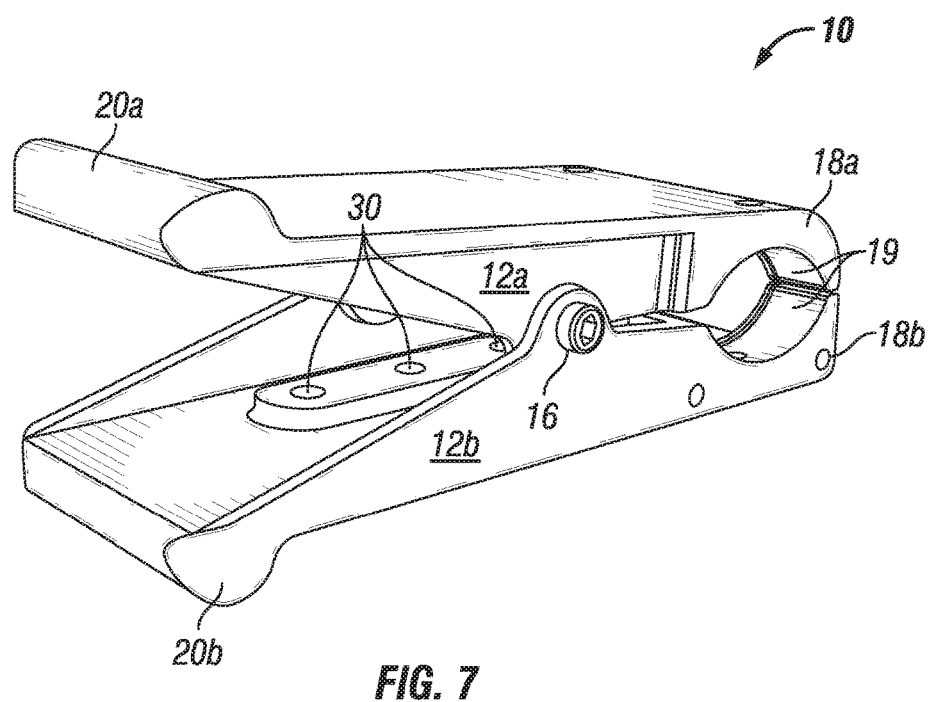
FIG. 7 is an isometric side view of a clamp assembly 10 with bracket 22 removed.

FIG. 7 is an isometric side view of a clamp assembly 10 with bracket 22 removed. As shown in this view, bracket 22 may be selectively attachable to the lever arm 12b through a bracket mounting portion 30. For example, bracket mounting portion 30 may comprise one or more threaded holes into which screws or bolts (not shown) may be inserted to fasten bracket 22 to the lever arm 12b. Other configurations are also possible.

As will be apparent, clamp assembly may be constructed of a variety of suitable materials. For example, clamp assembly may be manufactured out of metal, plastics, Fiberglas, composites, wood, glasses, polymers, rubber, and combinations of the foregoing.

Although various embodiments have been shown and described, the present disclosure is not so limited and will be understood to include all such modifications and variations are would be apparent to one skilled in the art.

What is claimed is:

1. An IV pump support clamp assembly comprising:
   a first lever arm comprising a back side that defines a first plane comprising a longitudinal axis having a proximal end and a distal end, a normal axis extending perpendicularly outward from the first plane, and a first clamping end, located at the proximal end, and curved to clamp a substantially circular cross-section support;
   a second lever arm comprising a second clamping end that is reciprocally curved with respect to the curve of the first clamping end;
   a central axle that connects the first lever arm and the second lever arm and enables the first clamping end and the second clamping end to pivot away and towards each other;
   a biasing spring that biases the first clamping end towards the second clamping end; and
   a bracket comprising:
      a clamp mounting portion connected to the back side of the first lever arm at a substantially perpendicular angle with respect to the normal axis of the first plane, and along the longitudinal axis near the distal end;
      a pump mounting portion located near the proximal end and in contact with the clamp mounting portion, spaced apart from the clamp mounting portion along the longitudinal axis towards the proximal end, and spaced away from the clamp mounting portion in the direction of the normal axis, and that enables an IV pump to be mounted thereon; and
      wherein the pump mounting portion is oriented at a non-zero angle with respect to the first plane.

2. The IV pump support clamp assembly of claim 1 further comprising:
   a first lip on an end of the first lever arm near the distal end and opposite the first clamping end;
   a second lip on an end of the second lever arm that is opposite the second clamping end; and
   wherein the first lip extends out from the first plane.

3. The IV pump support clamp assembly of claim 1 further comprising:
   a gripping element located in at least one of the first clamping end or the second clamping end.

4. The IV pump support clamp assembly of claim 1 wherein the clamp mounting portion and the pump mounting portions are oriented at an angle with respect to one another.

5. The IV pump support clamp assembly of claim 1 wherein the biasing spring is a torsional coil spring.

6. A clamp assembly comprising:
   a first lever arm comprising a back side that defines a first plane comprising a longitudinal axis having a proximal end and a distal end, a normal axis extending perpendicularly outward from the first plane, and a first clamping end located at the proximal end;
   a second lever arm comprising a second clamping end;
   a central axle that connects the first lever arm and the second lever arm and enables the first clamping end and the second clamping end to pivot away and towards each other;
   a biasing spring that biases the first clamping end towards the second clamping end; and
   a bracket connected to the first lever arm at a clamp mounting portion in contact with the back side of the first lever arm at a substantially perpendicular angel with respect to the normal axis of the first plane, and along the longitudinal axis near the distal end and wherein the bracket further comprises:
      a pump mounting portion located near the proximal end and in contact with the clamp mounting portion, spaced apart from the clamp mounting portion along the longitudinal axis, and spaced away from the clamp mounting portion in the direction of the normal axis, and that enables an IV pump to be mounted thereon; and
      wherein the pump mounting portion is oriented at a non-zero angle with respect to the first plane.

7. The clamp assembly of claim 6 further comprising:
   a first lip on an end of the first lever arm near the distal end and opposite the first clamping end;
   a second lip on an end of the second lever arm that is opposite the second clamping end; and
   wherein the first lip extends out from the first plane.

8. The clamp assembly of claim 6 further comprising:
   a gripping element located in at least one of the first clamping end or the second clamping end.

9. The clamp assembly of claim 6 wherein the biasing spring is a torsional coil spring.

10. A clamp for an IV pump:
    a first lever arm comprising a back side that defines a first plane comprising a longitudinal axis having a proximal end and a distal end, a normal axis extending perpendicularly outward from the first plane, and a first clamping end located at the proximal end;
    a second lever arm comprising a second clamping end;
    a central axle that connects the first lever arm and the second lever arm and enables the first clamping end and the second clamping end to pivot away and towards each other;
    a biasing spring that biases the first clamping end towards the second clamping end; and
    a bracket comprising:
       a clamp mounting portion connected to the first lever arm along the longitudinal axis near the distal end;
       a pump mounting portion located near the proximal end and in contact with the clamp mounting portion, spaced apart from the clamp mounting portion along the longitudinal axis, and spaced away from the clamp mounting portion in the direction of the normal axis, and that enables an IV pump to be mounted thereon;
and wherein the pump mounting portion is oriented at a non-zero angle with respect to the first plane.

11. The clamp for an IV pump support of claim 10 further comprising:

a first lip on an end of the first lever arm near the distal end and opposite the first clamping end;
a second lip on an end of the second lever arm that is opposite the second clamping end; and
wherein the first lip extends out from the first plane.

12. The clamp for an IV pump of claim 10 further comprising:

a gripping element located in at least one of the first clamping end or the second clamping end.

13. The clamp for an IV pump of claim 10 wherein the clamp mounting portion and the pump mounting portions are oriented at an angle with respect to one another.

14. The clamp for an IV pump of claim 10 wherein the biasing spring is a torsional coil spring.

\* \* \* \* \*